United States Patent [19]

Collins et al.

[11] Patent Number: 4,932,865
[45] Date of Patent: Jun. 12, 1990

[54] CRYSTALLINE ORTHODONTIC BRACKET

[75] Inventors: Paul R. Collins, Washougal, Wash.; Larry R. Rothrock, Poway, Calif.

[73] Assignee: Union Carbide Chemicals and Plastics Company Inc., Danbury, Conn.

[21] Appl. No.: 220,303

[22] Filed: Jul. 18, 1988

[51] Int. Cl.⁵ .............................................. A61C 7/00
[52] U.S. Cl. ............................................ 433/8; 433/9
[58] Field of Search ......................................... 433/8, 9

[56] References Cited

U.S. PATENT DOCUMENTS

| | | | |
|---|---|---|---|
| 4,219,617 | 8/1980 | Wallshein | 433/8 |
| 4,595,598 | 6/1986 | De Luca et al. | 433/8 |
| 4,639,218 | 1/1987 | Jones et al. | 433/8 |
| 4,681,538 | 7/1987 | De Luca et al. | 433/9 |
| 4,838,786 | 6/1989 | Reher et al. | 433/9 |

Primary Examiner—John J. Wilson
Assistant Examiner—Michael Lynch
Attorney, Agent, or Firm—Morris N. Reinisch

[57] ABSTRACT

A sapphire orthodontic bracket with enhanced tolerance to fabrication, installation and use is fabricated such that the "r" planes of the sapphire are at substantially equal angles to the longitudinal axis of the arch wire groove of the bracket.

9 Claims, 4 Drawing Sheets

CRYSTALLINE ORTHODONTIC BRACKET

The invention relates to an orthodontic bracket having tie wings and a base and being composed of a crystalline alpha alumina material having certain plane orientations with respect to the bracket.

BACKGROUND TO THE INVENTION

Orthodontic brackets attach directly to teeth and serve to transmit corrective forces from an orthodontic archwire to the tooth to which the bracket is attached. The requirements for an orthodontic bracket are quite severe. First, it must have sufficient mechanical strength to withstand the forces to which it will be subjected, including the forces transmitted by an archwire, ligation forces, and mastication forces. Second, it must be chemically inert in the oral environment so that it will not corrode and will be and remain biologically inert. The bracket must meet these requirements, and still remain small enough to fit on the tooth.

The overwhelming majority of orthodontic brackets in use today are made of metal, usually stainless steel. Metal brackets meet all of the essential requirements, but they have one undesirable attribute—they are unsightly. A person undergoing orthodontic treatment has a conspicuous amount of metal in full view on the front surfaces of his or her teeth. And since the treatment extends over a number of years, this unsightly appearance must be endured for a considerable period of time.

The incentive to make brackets from less unsightly materials has existed for many years. But recently, orthodontic treatment has been given to increasing numbers of adults, for whom the unsightly appearance of metal brackets is more than a mere annoyance. Ceramic brackets have been proposed but have a tendency to stain, especially if the bracket must be worn for extended periods of time. Therefore, the incentive to provide more esthetic orthodontic treatment is even greater now than it has ever been.

Recently, sapphire (crystalline alpha-alumina) has found commercial application as the material of construction for orthodontic brackets. U.S. Pat. No. 4,639,218 discloses sapphire orthodontic brackets, and sapphire orthodontic brackets are currently manufactured and sold by "A" Company, Inc., a subsidiary of the Johnson & Johnson Company, and Ormco Corporation. While these brackets are esthetically pleasing, i.e., are transparent and do not stain, concerns exist about the durability of the brackets made from sapphire under the considerable stresses on the bracket induced by the arch wire, ligation and mastication. Sapphire is more subject to fracturing and chipping than metal. Not only is this property undesirable from the standpoint of its use as an orthodontic bracket, but also, fractures and chips occurring during the fabrication of the bracket result in loss in yield.

Accordingly, it is desired to provide sapphire orthodontic brackets having enhanced resistance to fracturing and chipping during fabrication, installation and use.

BRIEF SUMMARY OF THE INVENTION

By this invention, crystalline alumina orthodontic brackets are provided that exhibit enhanced resistance to fracturing and chipping during fabrication, installation and use. Orthodontic brackets comprise a body having a base face (the side intended to face the tooth); a front face on the side opposing the base face, the front face defining a longitudinal arch wire groove; upper and lower sides extending between the base face and front face and edge faces between which faces the arch wire groove extends. In accordance with this invention, the orthodontic bracket is fabricated from crystalline alumina stock in which the axis of each "r" plane of the crystalline alumina is at an angle of between about 45° and 65° with respect to the longitudinal axis of the arch wire groove. Advantageously, the longitudinal axis of the arch wire groove either is (a) substantially normal ±10° to a plane passing through the intersection of a "c" plane and an "m" plane and having an axis of 20° with respect to the "c" plane, or (b) substantially normal, e.g., within about ±10°, of the "c" plane.

DETAILED DESCRIPTION OF THE INVENTION

As used herein, the term "crystalline alumina" is intended to include only essentially monocrystalline alumina, that is, alumina comprised of a single crystal or two or more single crystals grown together longitudinally but separated by a relatively small angle (usually within 4°, determined with respect to the "c" axes of neighboring single crystals) grain boundary. Most preferably, these grain boundaries do not vary by more than about 1°.

The crystalline alumina may solely consist of aluminum and oxygen atoms or may contain minor amounts of impurities or dopants, i.e., metal elements other than aluminum, which become incorporated into the crystalline framework. For purposes of ease of understanding, the following description will refer to the crystalline alumina as sapphire and such reference is not intended to limit the generality of the invention to other alumina-containing materials having the corundum crystal structure.

Figure 3:
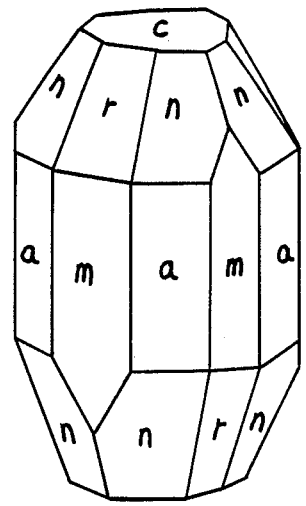
FIG. 3 is a perspective view of the various crystal planes of sapphire.

Sapphire is characterized as having a number of crystalline planes. FIG. 3 depicts in a perspective rendition the orientation of the various planes in a sapphire crystal. These planes include the "a" plane, "c" plane, "m" plane, "n" plane and "r" plane. It is generally known that the crystal structure is weaker along "r" planes than along the remaining crystal planes, which remaining planes have approximately the same strengths.

Sapphire stock can be produced by various techniques from molten alumina. One technique is the EFG (for Edge defined, Film-fed, Growth) technique which is a modification of the Czochralski process for growing crystalline alpha-alumina. The EFG process is the preferred process described in U.S. Pat. No. 4,639,218 for making a crystalline alpha alumina rod having a cross sectional configuration approximating that of an orthodontic bracket. The EFG process is described by La- Belle in "EFG—The Invention and Application to Sapphire Growth", in Journal of Crystal Growth, 50, pages 8-17 (Sept. 1980). See also LaBelle, U.S. Pat. No. 3,591,348, LaBelle et al., U.S. Pat. Nos. 3,701,636 and 3,915,662, and other patents and articles cited in the Journal of Crystal Growth article.

Another technique is the Czochralski process in which a single crystal boule of sapphire is drawn from a melt. This process is described, for instance, in U.S. Pat. No. 3,715,194. The boules may be sliced to provide flat stock material for fabrication. Flat stock material of various crystal planes is commercially available from Union Carbide Corporation, Danbury, Ct.

Although the EFG technique can provide the advantage of a near net cross sectional shape, the Czochralski technique is typically preferred to provide sapphire stock material for orthodontic brackets. There are several reasons for this preference. The Czochralski technique does not involve the use of any dies as does the EFG technique. The dies, which operate at the high temperatures of the alumina melt, can be a source of contaminants to the sapphire stock. These contaminants can adversely affect the light transmission and/or color quality of the sapphire. Also, the EFG technique is prone to inducing more strain within the crystal structure. Thus, as set forth in U.S. Pat. No. 4,639,218, the EFG technique crystal is preferably grown such that the "c" plane axis is perpendicular to the longitudinal axis of the rod. Undue strains within the sapphire crystal will, of course, increase the risk of undesirable breakage during fabrication of the orthodontic bracket, its installation and use. Even with growth in the preferred crystal orientation for the EFG technique, additional steps have been suggested to minimize breakage during fabrication. For instance, in U.S. Pat. No. 4,639,218, an annealing procedure is disclosed in which the bar stock from the EFG technique is heated from room temperature up to 1850° C at an even rate for 12 hours and then the 1850° C temperature is maintained for 4 to 6 hours followed by cooling at an even rate for 18 to 24 hours, to relieve stresses in the crystal to minimize the chances of breakage during machining. Another problem which usually occurs in greater frequency with the EFG technique than the Czochralski technique is the inclusion of defects within the crystal structure such as bubbles. Moreover, the bar stock from the EFG technique generally has exterior ridges or waves caused by the interaction of the die and the alumina, the surface of which freezes as it passes through the die.

Figure 1:
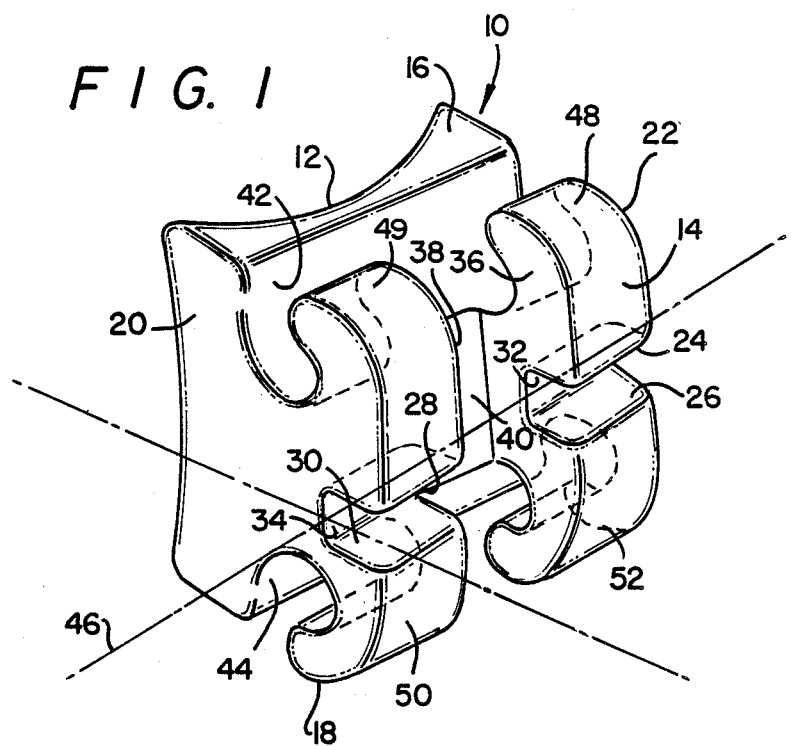
Fig. 1 is a perspective view of an orthodontic bracket made of crystalline alpha-alumina.

With reference to FIG. 1, an orthodontic bracket 10 having two pair of tie wings is fabricated completely of sapphire. The bracket has base face 12 which is depicted as being concave to fit the curvature of the tooth. Front face 14 is that face seen when directly looking at the mouth of the patient. Front face 14 may be parallel to the plane generally defined by the base face; however, the front face and the base face are typically at an angle of up to about 15° with respect to each other to facilitate the function of the orthodontic bracket. The bracket also defines top side 16 and bottom side 18 and edges 20 and 22. As can readily be seen from the FIG., the faces and sides can be curved. For the sake of the ease of understanding, the top and bottom faces, sides and edge faces referred to herein may be described as being in a plane. The plane referenced is that most closely characteristic of the orientation of the face, side or edge to which reference is being made.

The dimensions of the bracket may vary. Usually, the width (average distance between the faces) is between about 1 and 5 millimeters, the height (average distance between the planes of the top and bottom sides) is between about 1 and 5 millimeters, and the thickness (average distance between the planes of the front and back faces) is between about 1 and 4 millimeters. The dimensions are selected from functional and aesthetic standpoints.

Figure 6:
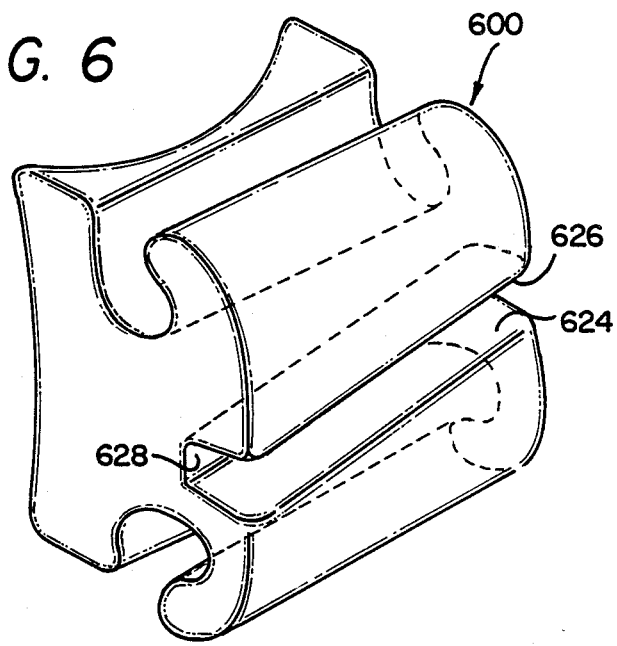
FIG. 6 is a perspective view of a "single wing" orthodontic bracket.

The front face defines an arch wire groove which extends between edge faces 20 and 22. The arch wire groove is defined by walls 24, 26, 28, 30, 32, 34, and the "saddle" defined by walls 36, 38, 40 of a double tie wing, or twin, bracket (such as is shown in FIG. 1). A single wing bracket 600 is shown in FIG. 6. In the single wing bracket 600 the archwire groove is defined by walls 624, 626 and 628 and no saddle exists. The arch wire groove may extend normal to the axis of an edge face or at an angle thereto, e.g., up to about 20°, for purposes of enhancing the function of the orthodontic bracket. The edge faces are depicted as being at right angles to the top and bottom sides; however, the edge faces and sides may form a structure having a trapezoidal cross-sectional configuration, e.g., a parallelogrammic or rhombohedric cross-section, in which case, the arch wire groove is often substantially parallel to the planes defined by the top and bottom surfaces. See, for instance, U.S. Pat. No. 4,415,330.

The arch wire groove is sized to receive the arch wire extending between teeth. Accordingly, the groove is relatively small, often about 0.4 to 0.6 (typically about 0.5) millimeter in depth. The bottom surface 34 of the arch wire groove is normally flat due to machinery considerations although curved configurations can be used. The bottom surface 34 of the arch wire groove can be equidistant from the front face or may be closer to the front face at certain regions than others. The particular design will depend upon the designer and the sought function. For the purposes of the description herein, the longitudinal axis 46 of the arch wire groove shall be the axis most closely characterized by the arch wire groove.

The top and bottom sides have surfaces 42 and 44, respectively, which define the tie wing sections 48, 49, 50 and 52 of the orthodontic bracket. As depicted in FIG. 1, surfaces 42 and 44 are indentations in the top and bottom sides. Alternatively, the tie wings may extend outwardly from the top and bottom surfaces. The tie wings are most often the portions of the orthodontic bracket to break during fabrication as well as during installation and use. The breaks may involve a cleavage between the bottom surface of the arch wire groove and the indentation defined by either surface 42 or 44, or alternatively may involve chipping of the tips of the tie wings (especially during machining). The orientation of the sapphire crystal in accordance with this invention reduces incidence of breakage.

The machining of the orthodontic bracket may be effected by any suitable technique. Often blanks are prepared and then by a series of cutting, grinding, and polishing steps the bracket is fabricated. A diamond cutting wheel can be used to cut out the archwire groove. Edges may be beveled by grinding, and corners rounded off by polishing. Subsequent annealing treatments can also be used.

The brackets are preferably polished after annealing to smooth off contours and to remove any surface imperfections which could encourage propagation of cracks. A flux polishing procedure can be used. The flux can be partially saturated with alumina so that the removal of alumina from the surface of the bracket will proceed at a controllable rate. One flux is composed of 51.2 percent $LiBO_2$, 12.8 percent $Li_2B_4O_7$, 16 percent $Al_2O_3$, and 20 percent LiF (the percentages are by weight). The machined brackets are immersed in molten flux at 850° C to 900° C for a few minutes, e.g., from about four to about thirty minutes, and then removed. After cooling, the brackets can be immersed in aqueous hydrofluoric acid to remove any flux adhering to the surfaces of the brackets.

Other processes for polishing the surface of crystalline alpha-alumina objects include those disclosed, for example, by Noble, in U.S. Pat. No. 4,339,300, and Manasevit, in U.S. Pat. No. 3,546,036.

By this invention, certain crystal orientations are provided with respect to the bracket geometry to enhance the ability to fabricate, install and use the orthodontic bracket. As can be perceived from the foregoing discussion, the machining required to form the orthodontic bracket can be complex and involves many different forces. Breakage most often occurs during machining. Moreover, the stresses placed on the bracket during installation and use are also complex. The most severe stresses occur during installation and adjustments, but the forces that are produced during mastication can also be formidable.

Figure 2:
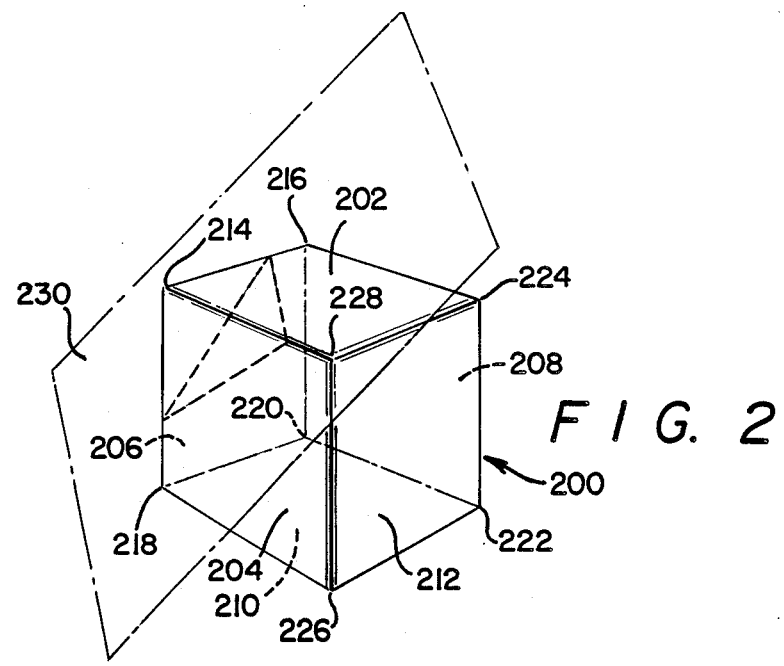
Fig. 2 is a perspective view of intersecting "r" planes in sapphire crystals.

In accordance with this invention, the sapphire stock is oriented such that the axis of each "r" plane of the sapphire crystal is at an angle of between about 45° and 65°, preferably 50° and 60°. with respect to the longitudinal axis of the arch wire groove. FIG. 2 is a representation of "r" planes in sapphire. The "r" planes form a generally cubic crystal 200 having plane 202 defined within corners 214, 216, 224 and 228; plane 204 defined within corners 214, 218, 226 and 228; plane 206 defined within corners 214, 216, 218 and 220; plane 208 defined within corners 216, 220, 222 and 224; plane 210 defined within corners 218, 220, 222 and 226; and plane 212 defined within corners 222, 224, 226 and 228. Preferably, the longitudinal axis 46 of the arch wire groove substantially intersects at least two of the following pairs of corners: 214 and 222; 216 and 226; 218 and 224; and 220 and 228. By substantially intersects, it is meant that longitudinal axis 46 is within about 10°, preferably about 5°, of the axis passing through any of the aforementioned sets of pairs of corners.

Due to the geometries of the "r" planes, the planes substantially intersecting at the longitudinal axis 46 will pass through a plane normal to the longitudinal axis of the arch wire groove in the pattern of a triangle. This cross sectional plane is generally depicted as plane 230 in FIG. 2 and the dotted line indicates the triangular area of intersection.

Prior to this invention, the sapphire orthodontic brackets that have been commercially available are believed by us to be made from "r"-plane blanks and thus an "r"-plane would generally be parallel to the front face 14 of the bracket or from EFG technique grown material in which the edge face was an "m" plane and the "c" plane extended substantially perpendicularly between the front and back faces parallel to the longitudinal axis of the arch wire groove. In such configuration, cleavage of the tie wings at the arch wire groove and/or chipping of the corners of the tie wings, especially during fabrication, can occur due to the orientation of "r" planes.

Figure 4:
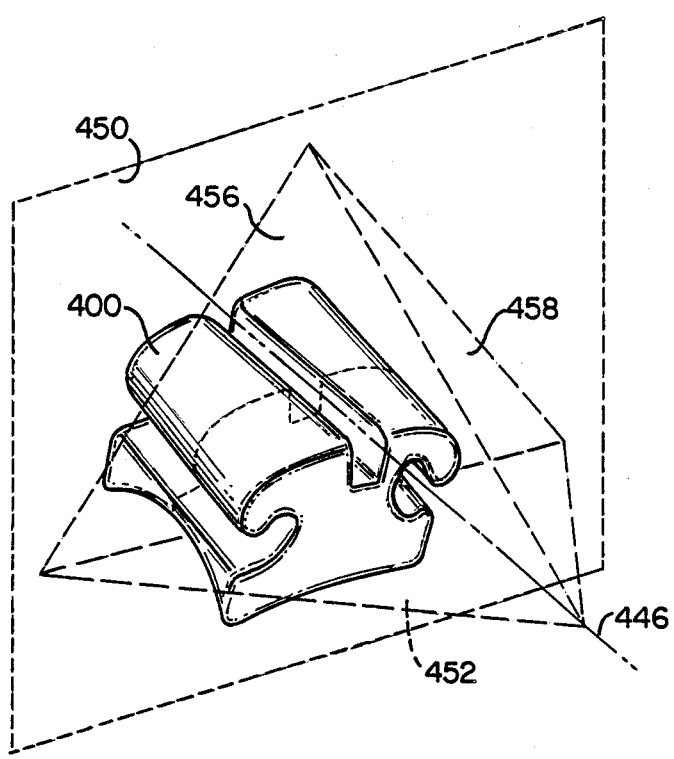
FIG. 4 is a perspective view of an orthodontic bracket depicting a "c" plane perpendicular to the longitudinal axis of the arch wire groove.

FIG. 4 depicts an orthodontic bracket 400 in which the "c" plane is normal to the longitudinal axis 446 of the arch wire groove. Superimposed on this perspective view are the orientations of the "c" plane 450 and the "r" planes 452, 458 and 456.

Figure 5:
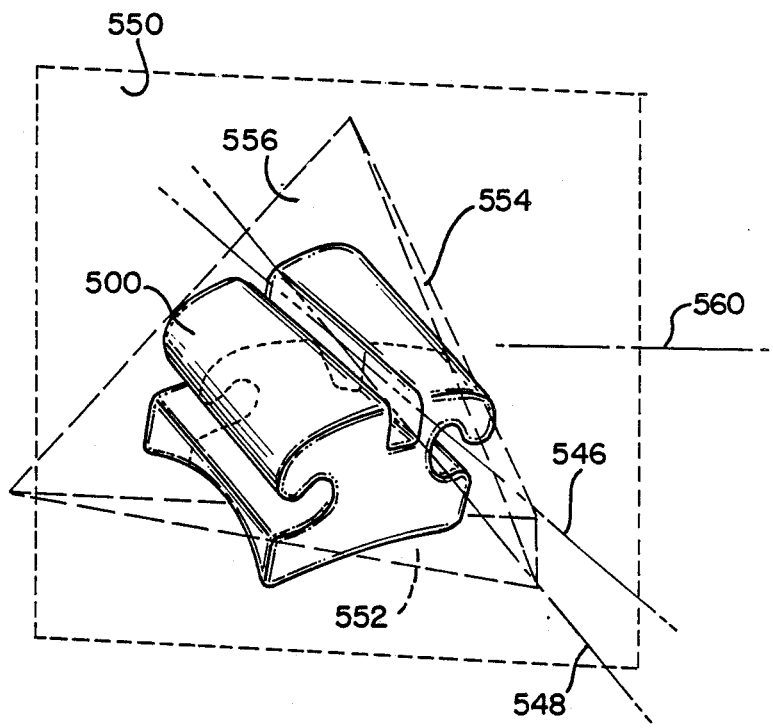
Fig. 5 is a perspective view of an orthodontic bracket depicting a cross-section oblique to the "m" plane.

FIG. 5 is another perspective view of an orthodontic bracket 500 in which the "m" plane 550 is depicted. Axis 560 is the axis of the "c" plane. The "r" planes 552, 554 and 556 are depicted as intersecting axis 548 which is at a small angle to the longitudinal axis 546 of the arch wire groove.

The "r" plane orientations of the present invention provide desirable resistance for cleavage of the tie wings at the arch wire groove while providing resistance to tie wing chipping. Preferably, the "r" planes are oriented such that a corner of the cube formed by the "r" planes is within 30°, preferably 20°, of the plane extending from the axis of the arch wire groove in a direction perpendicular to the plane of the front face of the bracket.

In alternative embodiments of the invention, the most critical load bearing portions of the bracket are made of a crystalline alumina material, while the remainder is made of another transparent material, such as polycarbonate or polysulfone plastic, that is less expensive, easier to work, and easier to bond to the tooth.

Bonding a crystalline alumina bracket to the tooth (or to a plastic base or to any other substrate) must be done with care. Many of the ordinary orthodontic cements (which are usually acrylic resins) will not adhere well to crystalline alumina without taking steps to enhance the adhesion. One means of enhancing the adhesion of a crystalline alumina bracket to the tooth is illustrated in Figs. 13 and 14 of U.S. Pat. No. 4,639,218 in which a bracket is shown that has an undercut or keyway in the back face of the bracket. Orthodontic cement filling the keyway will have enhanced mechanical adhesion to the bracket because of the undercut portion. The undercuts can also serve as slots for the insertion of pliers or the like for the orthodontic treatment.

Another means of enhancing the adhesion of cements such as acrylic resins to a crystalline alumina bracket is to alter the surface of the crystalline alumina in such a way as to increase the strength of the adhesive bond between the crystalline alumina and the cement. It is known, for instance, that a wide variety of silicone coupling agents can be used to enhance the adhesive force between siliceous substrates and a wide variety of thermosetting plastics. This technology may be utilized by coating the crystalline alumina surface that is to be in contact with the cement with a thin coating (usually thinner than about 10,000 angstroms, and preferably, up to about 1,000 angstroms) of a siliceous material such as silica, and then using silicone or silane coupling agents to enhance the bond of that surface to the cement, in a manner analogous to that which is presently known. Examples of means for coating the crystalline alumina surface with a siliceous material are cathode sputtering, plasma deposition, and electron beam evaporation, all of which are known techniques, especially in the semiconductor arts.

The crystalline alumina bracket having its base or tooth-contacting surface sputter coated with silica or other siliceous material such as a glass, has excellent affinity for silicone coupling agents such as A-174 (gamma-methacryloxypropyltrimethoxy silane), and by using such coupling agents the adhesion of the bracket to acrylic orthodontic cements is enhanced.

Another method for enhancing the affinity of the crystalline alpha-alumina bracket to silicone coupling agents is to heat the brackets to remove adsorbed water, and then treat the bracket with a dilute solution (e.g., a 2 to 2.5 weight per cent solution in toluene/propylene glycol monomethyl ether) of a silane coupling agent such as A-174.

The orthodontic brackets of the invention have enhanced esthetics because of the transparency of sapphire. For instance, the transparency of crystalline sapphire is such that a total of up to 98.5 per cent of light in the visible range is transmitted through it, as determined by the integrating sphere method.

The yield strength of the steel that is used to make orthodontic brackets is typically about 35,000 to 40,000 psi. The modulus of rupture of sapphire used in the invention is at least 35,000 to 40,000 and is often as high as about 100,000 psi. Therefore, the effective strength of the brackets of the invention is at least as high as that of the usual steel bracket and often much higher, but with significantly enhanced esthetics. (The modulus of rupture is determined at 25° C by the test procedure of ATM C-674).

A particularly useful test for evaluating orthodontic brackets is to insert a flat blade into the arch wire groove and twist the blade around an axis perpendicular to the longitudinal axis of the arch wire groove. The greater the force required to fracture the bracket, the better the crystal orientation within the bracket.

It is claimed:

1. An orthodontic bracket comprising a body comprising crystalline alpha-alumina having a base face intended to face a tooth and an opposing front face defining a longitudinal arch wire groove in which the axis of each "r" plane of the crystalline alpha alumina is at an angle of between about 45° and 65° with respect to the longitudinal axis of the arch wire groove.

2. The orthodontic bracket of claim 1 wherein said bracket is made entirely of crystalline alpha-alumina.

3. The orthodontic bracket of claim 1 wherein said crystalline alpha-alumina is sapphire.

4. The orthodontic bracket of claim 1 having at least one pair of tie wings.

5. The orthodontic bracket of claim 1 wherein said bracket has a rhomboidal configuration when viewed looking directly at the front of the bracket.

6. The orthodontic bracket of claim 1 wherein the archwire groove is oriented essentially parallel to the top and bottom faces of the bracket.

7. The orthodontic bracket of claim 1 wherein three "r" planes intersect substantially at an axis parallel to the longitudinal axis of the arch wire groove.

8. The orthodontic bracket of claim 1 wherein the longitudinal axis of the arch wire groove is substantially normal to a "c" plane of the crystalline alpha-alumina.

9. The orthodontic bracket of claim 1 wherein the longitudinal axis of the arch wire groove is at an angle of between about 60° to 80° with respect to an "m" plane of the crystalline alpha-alumina.

* * * * *